United States Patent

Cliffe et al.

[11] Patent Number: 5,827,847
[45] Date of Patent: Oct. 27, 1998

[54] TREATMENT OF COGNITIVE DISORDERS WITH PIPERAZINE DERIVATIVES

[75] Inventors: Ian Anthony Cliffe; Allan Fletcher, both of Slough; Alan Chapman White, Staines, all of England

[73] Assignee: John Wyeth & Brother, Ltd., Maidenhead, England

[21] Appl. No.: 428,093

[22] PCT Filed: Oct. 25, 1993

[86] PCT No.: PCT/GB93/02197

§ 371 Date: May 3, 1995

§ 102(e) Date: May 3, 1995

[87] PCT Pub. No.: WO94/09780

PCT Pub. Date: May 11, 1994

[30] Foreign Application Priority Data

Nov. 5, 1992 [GB] United Kingdom .................. 9223153

[51] Int. Cl.⁶ .................. A61K 31/55; A61K 31/395; A61K 31/535; A61K 31/495

[52] U.S. Cl. .................. 514/212; 514/210; 514/235.8; 514/252; 514/255

[58] Field of Search .................. 514/212, 210, 514/235.8, 252, 255

[56] References Cited

U.S. PATENT DOCUMENTS

| | | | |
|---|---|---|---|
| 4,423,049 | 12/1983 | Temple | 424/251 |
| 4,921,958 | 5/1990 | Abou-Gharbia et al. | 544/295 |
| 4,988,814 | 1/1991 | Abou-Gharbia et al. | 544/295 |

FOREIGN PATENT DOCUMENTS

| | | |
|---|---|---|
| A1390424 | 3/1990 | European Pat. Off. . |
| A1398413 | 5/1990 | European Pat. Off. . |
| A14039631 | 6/1992 | Germany . |
| 1567845 | 5/1980 | United Kingdom . |
| A2222768 | 3/1990 | United Kingdom . |
| A2230780 | 10/1990 | United Kingdom . |
| A2230781 | 10/1990 | United Kingdom . |
| A2248836 | 4/1992 | United Kingdom . |
| A22255337 | 11/1992 | United Kingdom . |
| WO9111435 | 8/1991 | WIPO . |
| WO9304681 | 3/1993 | WIPO . |

OTHER PUBLICATIONS

Costall, B. et al., *Pharmacopsychiatry* 23/SU 2:85–89 (1990).

Murphy, D. L., *Neuropsychopharmacology* 3:457–471 (1990).

Rydelek–Fitzgerald, L. et al., *Brain Research* 532:191–196 (1990).

Winter, J. C. et al., *Pharmacology Biochemistry & Behavior* 27:625–628 (1987).

Hunter, A. J. et al., *Behavioural and Neurochemical Pharmacology* 22:278–285, 1987.

Ogren, S. O., *Biology of Seortonergic Transmission* 13:317–334 (1982).

*Primary Examiner*—William R. A. Jarvis
*Attorney, Agent, or Firm*—Arthur G. Seifert

[57] ABSTRACT

Piperazine derivatives of formula (I) are useful in the treatment of cognitive disorders. In formula (I), X is a group of (IIa): —$(CH_2)_n CR^2 R^3 CONR^4 R^5$ or (IIIb): —$A—NR^6 COR^7$ where n, A, R, $R^1$, $R^2$, $R^3$, $R^4$, $R^5$, $R^6$ and $R^7$ have specified meanings.

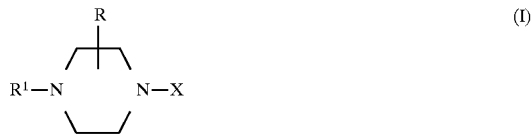

3 Claims, No Drawings

TREATMENT OF COGNITIVE DISORDERS WITH PIPERAZINE DERIVATIVES

This application is a 371 of PCT/GB93/02197, filed Oct. 25, 1993.

This invention relates to the use of certain piperazine derivatives in the treatment of cognitive disorders The piperazine derivatives are those of general formula

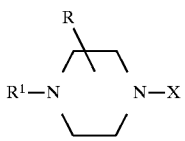
(I)

and the pharmaceutically acceptable acid addition salts thereof

In formula (I)
R is hydrogen or lower alkyl,
$R^1$ an aryl or nitrogen containing heteroaryl radical,
and X is a group of formula

 (IIa)

or

 (IIb)

where
n is one of the integers 1 or 2,
$R^2$ is hydrogen or lower alkyl,
$R^3$ is an aryl radical or an aryl(lower)alkyl radical,
$R^4$ is hydrogen or lower alkyl,
$R^5$ is hydrogen, an alkyl group of 1 to 8 carbon atoms, cycloalkyl of 3 to 12 carbon atoms or cycloalkyl(lower) alkyl,
or $R^4$ and $R^5$ together with the nitrogen atom to which they are attached represent an azetidino, pyrrolidino, piperidino, hexahydroazepino, morpholino or piperazino ring which may be optionally substituted by lower alkyl, aryl or aryl(lower)alkyl, A is an alkylene chain of 2 to 4 carbon atoms optionally substituted by one or more lower alkyl groups,
$R^6$ is a mono or bicyclic heteroaryl radical
and $R^7$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^8R^9$ [where $R^9$ is hydrogen, lower alkyl, aryl or aryl(lower)alkyl and $R^{10}$ is hydrogen, lower alkyl, —CO(lower)alkyl, aryl, COaryl, aryl(lower)alkyl, cycloalkyl or cycloalkyl(lower)alkyl or $R^8$ and $R^9$ together with the nitrogen atom to which they are both attached represent a saturated heterocyclic ring which may contain a further hetero atom] or a group of formula $OR^{11}$ [where $R^{11}$ is lower alkyl, cycloalkyl, cycloalkyl (lower)alkyl, aryl, aryl(lower)alkyl, heteroaryl or heteroaryl (lower)alkyl].

Preferred compounds of formula I are those of

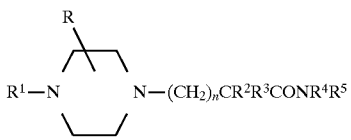 (II)

or the pharmaceutically acceptable acid addition salts thereof (where n, R, $R^1$, $R^2$, $R^3$, $R^4$ and $R^5$ are as defined above).

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert-butyl, pentyl and isopentyl. Examples of cycloalkyl groups are cyclopentyl, cyclohexyl and cycloheptyl. A preferred example is cyclohexyl. Cycloalkyl groups include bicyclic, tricyclic and tetracyclic groups, e.g. adamantyl. Preferably the cycloalkyl group contains 3 to 12 carbon atoms.

When used herein "aryl" means an aromatic radical having 6 to 12 carbon atoms (e.g. phenyl or naphthyl) which optionally may be substituted by one or more substituents. Preferred substituents are lower alkyl, lower alkoxy (e.g. methoxy, ethoxy, propoxy, butoxy), halogen, halo(lower) alkyl (e.g. trifluoromethyl), nitro, nitrile, amido, (lower) alkoxycarbonyl, amino, (lower)alkylamino or di(lower) alkylamino substituents. Two substituents on the aromatic ring may be connected together to form another ring system.

When $R^1$ is an aryl radical it is preferably a phenyl radical containing a substituent in the ortho position. A preferred example of $R^1$ is o-(lower)alkoxyphenyl e.g. o-methoxyphenyl. $R^1$ can also be, for example a 1-naphthyl radical optionally substituted in the 2 or 7 positions by, for example, (lower)alkoxy.

Preferred examples of aryl(lower)alkyl are benzyl and phenethyl in which the phenyl rings may be substituted by substituents as given above.

When used herein "nitrogen containing heteroaryl radical" means an aromatic ring containing one or more nitrogen atoms as heteroatoms (e.g. pyridinyl, pyrimidinyl or pyrazinyl) which may optionally be substituted by one or more lower alkyl, lower alkoxy, halogen, trifluoromethyl, amino, (lower)alkylamino or di(lower)alkylamino substituents. Preferably the heteroaryl radical is monocyclic.

When $R^6$ is a bicyclic heteroaryl radical both rings of the radical may contain hetero ring atoms or only one ring may contain a hetero atom or atoms. In the latter instance the radical $R^6$ is connected to the rest of the molecule of formula (I) via the ring containing the hetero atom(s).

Examples of the heteroaryl radical $R^6$ include monocyclic radicals containing one hetero atom, e.g. optionally substituted pyridyl (particularly 2-pyridyl), monocyclic radicals containing two hetero atoms, e.g. thiazolyl (particularly 2-thiazolyl) and bicyclic radicals containing one or two hetero atoms e.g. quinolinyl or isoquinolinyl (particularly 2-quinolinyl).

The piperazine derivatives of formula (I) and their method of preparation are disclosed, for example, in GB 2230780A
GB 2230781A
GB 2248836A and
GB 2255337A The compounds disclosed in GB 2230780A are described as antidepressant and/or anxiolytic agents. The compounds disclosed in GB 2230781A, GB 2248836A and GB 2255337A are disclosed as 5-$HT_{1A}$ antagonists useful for the treatment of CNS disorders such as anxiety, as antidepressants, hypotensives and as agents for regulating the sleep/wake cycle, feeding behaviours and/or sexual function.

The preferred compounds of formula (I) are:
N-tert-butyl-3-[4-(2-methoxyphenyl)piperazin-1-yl]-2-phenylpropanamide and its (S)-enantiomer
2,3,4,5,6,7-hexahydro-1-[4-[1-[4-(2-methoxyphenyl) piperazinyl]]-2-phenyl]butanoyl-1H-azepine
(−)-(R)-2,3,4,5,6,7-hexahydro-1-[4-[4-(2-methoxyphenyl)piperazin-1-yl]-2-phenyl]butanoyl-1H-azepine N-[2-[4-(2-methoxyphenyl)-1-piperazinyl]ethyl]-N-(2-pyridinyl)cyclohexanecarboxamide and their pharmaceutically acceptable acid addition salts.

The present provides in one aspect, a method of treating cognitive disorders which comprises administering to a human in need thereof an effective amount of a compound of formula (I) as defined above or a pharmaceutically acceptable acid addition salt thereof. In a second aspect the invention provides the use of a compound of formula (I) as defined above or a pharmaceutically acceptable acid addition salt thereof for the manufacture of a medicament for the treatment of cognitive disorders.

The compounds are useful in the treatment of cognitive disorders such as memory deficits and dementia states. Examples of such states occur, for example, in senile dementia (e.g. Alzheimer's disease), brain damage caused by stroke and brain injuries, and age associated memory impairment.

In this specification the terms "treatment" and "treating" relate to the administration of the compounds to prevent the disorder as well as to treat the disorder or to alleviate the symptoms of the disorder.

The efficacy of the compounds for treating congitive disorders can be examined in two ways. First, the influence of compounds on learning and memory in normal animals is examined by comparing the performance of compound-treated animals to vehicle treated control animals. Compounds that improve learning and memory are expected to enhance performance whereas compounds that interfere with learning and memory would be predicted to impair performance in the learning and memory tasks. Second, in an attempt to model specific diseases, learning and memory deficits can be experimentally-induced and the ability of target substances to reverse the resulting cognitive deficits examined. For example, in order induce cognitive deficits and to model the deficiency in central glutamatergic neurotransmission which occurs in Alzheimer's Disease, antagonists of glutamate receptors can be administered to animals which are then tested in a suitable behavioural procedure (e.g. the radial arm maze). In this procedure the selective 5-$HT_{1A}$ antagonist, (−)-(R)-2,3,4,5,6,7-hexahydro-1-[4-[4-(2-methoxyphenyl)piperazin-1-yl]-2-phenyl]butanoyl-1H-azepine, has been shown to reverse the cognitive deficits induced by the glutamate receptor antagonist, MK-801. Animals were required to learn and remember in which parts of the apparatus they could locate food rewards. The administration of MK-801 (0.1 mg/kg i.p.) significantly increased the number of errors made by the animals, compared to vehicle-pretreated controls. At doses of 0.3 and 3.0 mg/kg s.c., the 5-$HT_{1A}$ antagonist, (−)-(R)-2,3,4,5,6,7-hexahydro-1-[4-[4-(2-methoxyphenyl)-piperazin-1-yl]-2-phenyl]butanoyl-1H-azepine, significantly reversed the cognitive deficit induced by MK-801.

The compounds may be used in treating cognitive disorders in their free base form or as acid addition salts.

Examples of acid addition salts are those formed from inorganic and organic acids; such as sulphuric, hydrochloric, hydrobromic, phosphoric, tartaric, fumaric, maleic, citric, acetic, formic, methanesulphonic, p-toluenesulphonic, oxalic and succinic acids.

The compounds of formula I contain one or more asymmetric carbon atoms, so that the compounds can exist in different steroisomeric forms. The compounds can, for example, exist as racemates or optically active forms.

The compounds may be used for treating cognitive disorders in the form of pharmaceutical compositions which comprise a compound of formula I or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

| Preparation of Tablets | Amount per tablet mg | | |
|---|---|---|---|
| (−)-(R)-2,3,4,5,6,7-Hexahydro-1-[4-[4-(2-methoxyphenyl)piperazin-1-yl]-2-phenyl]butanoyl-1H-azepine | 1 | 5 | 10 |
| Microcrystalline cellulose | 49.25 | 47.25 | 44.75 |
| Modified food corn starch | 49.25 | 47.25 | 44.75 |
| Magnesium stearate | 0.5 | 0.5 | 0.5 |

Tablets are prepared from bulk amounts of ingredients in the proportions given above.

All of the active compound, cellulose and a portion of the corn starch are mixed and granulated to 10% corn starch paste. The resulting granulation is sieved, dried and blended with the remainder of the corn starch and the magnesium stearate. The resulting granulation is then compressed into tablets containing 1, 5 and 10 mg of the active ingredient per tablet.

EXAMPLE 2

| Preparation of powder filled capsules | Amount mg | |
|---|---|---|
| N-tert.butyl-3-[4-(2-methoxyphenyl)piperazin-1-yl]-2-phenylpropanamide | 10 | 15 |
| Avicel | 45 | — |
| Lactose | 153 | — |
| Starch (1500 NF) | — | 117 |
| Sodium starch glycollate | — | 6 |
| Magnesium stearate | 2 | 2 |

The formulations are prepared by admixing the ingredients in the proportions given above and filling two-part hard gelatin capsules with the required amount of the resulting mixture to give capsules containing 10 or 15 mg of the active compound.

We claim:

1. A method of treating cognitive disorders which comprises administering to a human in need thereof an effective amount of a piperazine derivative of general formula (I)

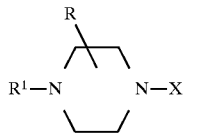
(I)

or a pharmaceutically acceptable acid addition salt thereof where R is hydrogen or lower alkyl, $R^1$ is an aryl or nitrogen containing heteroaryl radical, and X is a group of formula $$-(CH_2)_n CR^2R^3 \cdot CONR^4R^5 \qquad (IIa)$$

or $$-A-NR^6COR^7 \qquad (IIb)$$

where n is one of the integers 1 or 2, $R^2$ is hydrogen or lower alkyl, $R^3$ is an aryl radical or an aryl(lower)alkyl radical, $R^4$ is hydrogen or lower alkyl, $R^5$ is hydrogen, an alkyl group of 1 to 8 carbon atoms, cycloalkyl of 3 to 12 carbon atoms or cycloalkyl(lower) alkyl, or $R^4$ and $R^5$ together with the nitrogen atom to which they are attached represent an azetidino, pyrrolidino, piperidino, hexahydroazepino, morpholino or piperazino ring which may be optionally substituted by lower alkyl, aryl or aryl(lower)alkyl, A is an alkylene chain of 2 to 4 carbon atoms optionally substituted by one or more lower alkyl groups, $R^6$ is a mono or bicyclic- heteroaryl radical and $R^7$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula $-NR^8R^9$, where $R^9$ is hydrogen, lower alkyl, aryl or aryl(lower)alkyl and $R^{10}$ is hydrogen, lower alkyl, $-CO$(lower)alkyl, aryl, COaryl, aryl(lower)alkyl, cycloalkyl or cycloalkyl(lower)alkyl or $R^8$ and $R^9$ together with the nitrogen atom to which they are both attached represent a saturated heterocyclic ring which may contain a further hetero atom or a group of formula $OR^{11}$, where $R^{11}$ is lower alkyl, cycloalkyl, cycloalkyl (lower)alkyl, aryl, aryl(lower)alkyl, heteroaryl or heteroaryl(lower)alkyl.

2. A method as claimed in claim 1 wherein the compound of general formula (I) has the formula

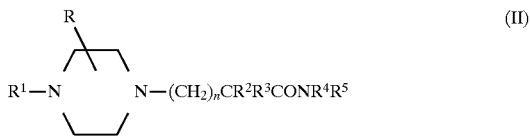
(II)

where n, R, $R^1$, $R^2$, $R^3$, $R^4$ and $R^5$ are as defined in claim 1.

3. A method as claimed in claim 1 wherein the compound of formula (I) is

N-tert-butyl-3-[4-(2-methoxyphenyl)piperazin-1-yl]-2-phenylpropanamide or its (S)-enantiomer or 2,3,4,5,6,7-hexahydro-1-[4-[1-[4-(2-methoxyphenyl) piperazinyl]]-2-phenyl]butanoyl-1H-azepine or (−)-(R)-2,3,4,5,6,7-hexahydro-1-[4-[4-(2-methoxyphenyl)piperazin-1-yl]-2-phenyl]butanoyl-1H-azepine or N-[2-[4-(2-methoxyphenyl)-1-piperazinyl]ethyl]-N-(2-pyridinyl)cyclohexanecarboxamide.

* * * * *